(12) United States Patent
Achtermann et al.

(10) Patent No.: US 11,926,963 B2
(45) Date of Patent: Mar. 12, 2024

(54) METHOD FOR DETERMINING THE DRYNESS OF A FIBROUS WEB, AND METHOD FOR CONTROLLING OR REGULATING A MACHINE FOR PRODUCING A PAPER WEB, AND COMPUTER PROGRAM FOR CARRYING OUT THE METHODS

(71) Applicant: VOITH PATENT GMBH, Heidenheim (DE)

(72) Inventors: Jan Achtermann, Horgenzell (DE); Marcus Schwier, Meckenbeuren-Brochenzell (DE); Marco Popp, Weismain (DE); Juergen Schaefer, Ravensburg (DE)

(73) Assignee: Voith Patent GmbH, Heidenheim (DE)

( * ) Notice: Subject to any disclaimer, the term of this patent is extended or adjusted under 35 U.S.C. 154(b) by 591 days.

(21) Appl. No.: 16/767,360

(22) PCT Filed: Nov. 20, 2018

(86) PCT No.: PCT/EP2018/081831
§ 371 (c)(1),
(2) Date: May 27, 2020

(87) PCT Pub. No.: WO2019/101701
PCT Pub. Date: May 31, 2019

(65) Prior Publication Data
US 2020/0385927 A1    Dec. 10, 2020

(30) Foreign Application Priority Data

Nov. 27, 2017   (DE) ...................... 10 2017 127 932.6

(51) Int. Cl.
*D21F 7/00*    (2006.01)
*D21F 5/18*    (2006.01)
(Continued)

(52) U.S. Cl.
CPC .............. *D21F 7/003* (2013.01); *D21F 5/181* (2013.01); *D21F 7/12* (2013.01); *D21F 11/14* (2013.01);
(Continued)

(58) Field of Classification Search
CPC .......... D21F 3/0218; D21F 7/003; D21F 5/00; D21F 5/044; D21F 5/18; D21F 5/181;
(Continued)

(56) References Cited

U.S. PATENT DOCUMENTS 4,639,291 A * 1/1987 Ota ......................... D21F 7/003
162/207
5,262,955 A * 11/1993 Lewis ..................... D21F 7/003
162/253
(Continued)

FOREIGN PATENT DOCUMENTS

CA        2336959 C  *  4/2008  ............. B65H 20/00
CH        617054 B   * 11/1980  ............... D04H 1/74
(Continued)

*Primary Examiner* — Jose A Fortuna
(74) *Attorney, Agent, or Firm* — Laurence A. Greenberg; Werner H. Stemer; Ralph E. Locher

(57) ABSTRACT

A method for determining the dryness of a fibrous web, in particular a tissue web, during the production of the fibrous web, is carried out in a machine including a drying cylinder, in particular a Yankee cylinder, to which at least one, preferably two, dryer hoods are assigned, and a reel-up for winding up the fibrous web. The determination of the dryness of the fibrous web is carried out before the drying cylinder on the basis of measured values which describe the following variables: the amount of solids in the fiber web at the reel-up, the amount of water in the fiber web at the reel-up, and the amount of water which is evaporated in the dryer hood or hoods. A method for controlling or regulating (Continued)

a machine for producing a fibrous web, a computer program and computer program product are also provided.

9 Claims, 1 Drawing Sheet

(51) Int. Cl.
    *D21F 7/12*       (2006.01)
    *D21F 11/14*     (2006.01)
    *D21G 9/00*       (2006.01)
    *D21H 27/00*     (2006.01)
    *G01N 33/34*     (2006.01)

(52) U.S. Cl.
    CPC .......... *D21G 9/0036* (2013.01); *D21H 27/002* (2013.01); *G01N 33/34* (2013.01)

(58) Field of Classification Search
    CPC .......... D21F 7/12; D21F 11/14; D21F 11/145; D21F 11/06; D21G 9/0036; D21H 27/002; G01N 33/34; Y10S 162/06
    See application file for complete search history.

(56) References Cited

U.S. PATENT DOCUMENTS

| | | | | |
|---|---|---|---|---|
| 5,465,504 A * | 11/1995 | Joiner | ...................... | D21F 5/044 |
| | | | | 34/551 |
| 5,718,060 A * | 2/1998 | Mori | ...................... | D21F 7/003 |
| | | | | 34/454 |
| 6,780,284 B2 * | 8/2004 | Almi | ...................... | D21F 7/003 |
| | | | | 162/263 |
| 7,691,228 B2 * | 4/2010 | Edwards | ................ | D21F 5/182 |
| | | | | 162/207 |
| 7,811,417 B2 * | 10/2010 | MacHattie | .............. | D21F 7/003 |
| | | | | 162/263 |
| 8,261,465 B2 * | 9/2012 | Mayer | .................. | D21G 1/0093 |
| | | | | 118/100 |
| 8,277,609 B2 * | 10/2012 | Hermans | ................ | D21F 11/14 |
| | | | | 242/160.1 |
| 9,121,136 B2 | 9/2015 | Aengeneyndt et al. | | |
| 9,284,686 B1 | 3/2016 | Lindsey et al. | | |
| 9,702,084 B2 * | 7/2017 | Saikkonen | .............. | D21F 5/181 |
| 9,873,981 B2 * | 1/2018 | Edbauer | ................ | D21G 3/005 |
| 10,260,200 B2 * | 4/2019 | Saikkonen | .............. | D21F 5/044 |
| 11,268,240 B2 * | 3/2022 | Saikkonen | .............. | D21F 5/044 |
| 2003/0222219 A1 * | 12/2003 | Almi | .................... | D21G 9/0027 |
| | | | | 250/341.1 |
| 2004/0118009 A1 | 6/2004 | Parent | | |
| 2006/0162887 A1 * | 7/2006 | Weinstein | ................. | D21F 3/02 |
| | | | | 162/263 |
| 2007/0151690 A1 * | 7/2007 | MacHattie | .............. | D21F 7/003 |
| | | | | 162/275 |
| 2008/0017341 A1 * | 1/2008 | Maenpaa | ................ | G01N 29/07 |
| | | | | 162/263 |
| 2008/0179028 A1 * | 7/2008 | Weinstein | ............... | D21F 7/003 |
| | | | | 162/184 |
| 2009/0056894 A1 * | 3/2009 | Hermans | ................. | D21F 11/14 |
| | | | | 162/119 |
| 2012/0267063 A1 * | 10/2012 | Klerelid | ................ | D21F 11/006 |
| | | | | 162/149 |
| 2015/0013927 A1 * | 1/2015 | Aengeneyndt | ....... | D21G 1/0286 |
| | | | | 162/252 |
| 2018/0266052 A1 * | 9/2018 | Kallerdahl | .............. | D21F 7/003 |
| 2018/0298555 A1 * | 10/2018 | Bjerke | ..................... | D21F 1/523 |
| 2020/0385927 A1 * | 12/2020 | Achtermann | ......... | D21F 11/006 |
| 2022/0042244 A1 * | 2/2022 | Saikkonen | .............. | D21F 5/181 |

FOREIGN PATENT DOCUMENTS

| | | | | |
|---|---|---|---|---|
| CN | 109964189 B | * | 8/2022 | ............. A01B 69/00 |
| DE | 102012203035 A1 | | 8/2013 | |
| DE | 102017127932 A1 | * | 5/2019 | ............ D21F 11/006 |
| DE | 102019123270 A1 | * | 3/2020 | ............. D21F 3/06 |
| EP | 808942 A2 | * | 11/1997 | ............ D21F 5/044 |
| EP | 2204491 A1 | * | 7/2010 | ............ D21F 7/003 |
| EP | 2418321 A1 | * | 2/2012 | ............ D21F 7/003 |
| EP | 3165673 A1 | * | 5/2017 | ............ D21F 5/181 |
| EP | 3378989 A1 | * | 9/2018 | ............ D21F 5/181 |
| EP | 3647491 A1 | * | 5/2020 | |
| EP | 3717695 B1 | * | 7/2021 | ............ D21F 11/006 |
| WO | WO-9925922 A1 | * | 5/1999 | ............. D21F 11/00 |
| WO | WO-0003087 A1 | * | 1/2000 | ............. B65H 20/00 |
| WO | WO-2019101701 A1 | * | 5/2019 | ............ D21F 11/006 |

* cited by examiner

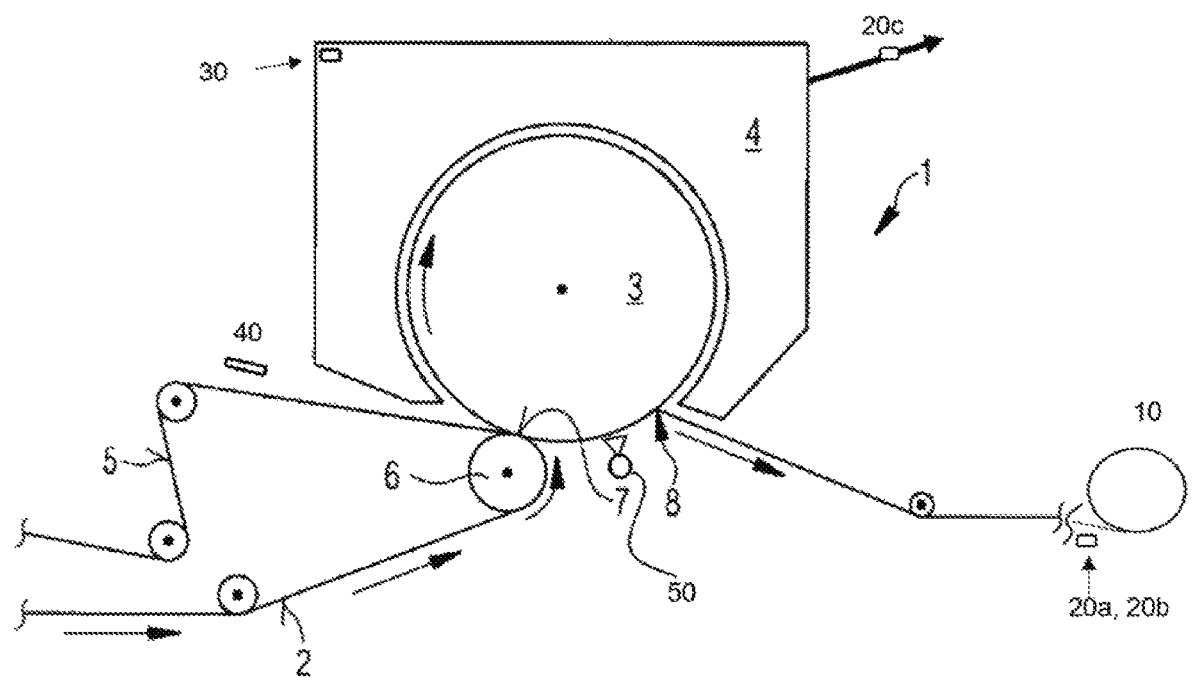

METHOD FOR DETERMINING THE DRYNESS OF A FIBROUS WEB, AND METHOD FOR CONTROLLING OR REGULATING A MACHINE FOR PRODUCING A PAPER WEB, AND COMPUTER PROGRAM FOR CARRYING OUT THE METHODS

BACKGROUND OF THE INVENTION

Field of the Invention

The invention comprises a method for controlling and/or regulating a machine for producing a fibrous web, in particular a tissue web, including a drying cylinder, in particular a Yankee cylinder, to which at least one, preferably two, dryer hoods are assigned, and a reel-up for winding up the fibrous web, and a method for determining the dryness of a fibrous web, in particular a tissue web, during the production of the fibrous web in a machine, wherein the machine includes a drying cylinder, in particular a Yankee cylinder, to which at least one, preferably two, dryer hoods are assigned, and a reel-up for winding up the fibrous web. The invention further relates to a computer program for carrying out such a method and computer program product having such a computer program.

A central element in the production of tissue webs—but also other fibrous webs—is what is known as a Yankee cylinder. This is a normally steam-heated cylinder with a comparatively large diameter, over which the fibrous web is guided to be dried. In addition, such a cylinder is further assigned at least one—frequently two—dryer hood/s. By means of one or more dryer hoods, air heated by gas and/or steam is brought to the surface of the fibrous web, in order to further accelerate the drying of the web. Such an apparatus is described, for example, in DE 10 2012 203 035.

In order to permit optimal operation of the machine, the temperature of said hot air must be matched to the nature of the fibrous web. For this purpose, the knowledge of the dryness of said fibrous web before the Yankee cylinder is an important characteristic variable.

The determination of the dryness of a fibrous web is generally complicated. For this purpose, taking a sample is normally necessary. From this sample, the dryness of the web is then determined in the laboratory. As a rule, it takes several hours to dry the samples completely and to determine the dryness. Control, and in particular regulation, by using such a measured value is barely possible.

In addition, taking this sample directly before the Yankee is very difficult, since there is the danger that either the surface of the Yankee cylinder and/or a felt of a press unit frequently arranged there will be damaged when taking the sample. In addition, taking the sample at these positions is also not without danger for the personnel, for which reason it is even not permitted on many machines for safety reasons.

SUMMARY OF THE INVENTION

It is an object of the invention to improve the possibility of controlling or regulating a machine for producing a fibrous web, in particular a tissue machine.

It is a further object of the invention to increase the safety for the operating personnel, specifically with regard to the taking of a sample, as compared with the prior art.

It is a further object of the invention to propose a control or regulating system which can be implemented economically and without great outlay.

The objects are completely achieved by a method for controlling or regulating a machine for producing a fibrous web in which the dryness of the fibrous web before the drying cylinder is used for the control or regulation, and a method for determining the dryness of the fibrous web in which the determination of the dryness of the fibrous web is carried out before the drying cylinder on the basis of measured values which describe the following variables: the amount of solids in the fibrous web at the reel-up, the amount of water in the fibrous web at the reel-up, and the amount of water which is evaporated in the dryer hood or hoods, a computer program for carrying out the method and a computer program product having the computer program.

With regard to the determination of the dryness of a fibrous web, the object is achieved by a method for determining the dryness of a fibrous web, in particular a tissue web, during the production of the fibrous web in a machine, wherein the machine comprises a drying cylinder, in particular a Yankee cylinder, to which one, preferably two, dryer hoods are assigned, and a reel-up for winding up the fibrous web, characterized in that the determination of the dryness of the fibrous web is carried out before the drying cylinder on the basis of measured values which describe the following variables:

a) amount of solids at the reel-up, b) amount of water at the reel-up, c) amount of water which is evaporated in the dryer hood or hoods.

Advantageous embodiments are described in the dependent claims. Usually, the amounts of fiber and the amounts of water to the variables according to a), b) and c) are measured and specified in k/h or in t/h. However, provision can also be made for the variables for a), b) and c) to be present in another form.

When, within the context of this application, mention is made of the fact that the dryness of the fibrous web is determined, it is clear to those skilled in the art in the field that the moisture content of the fibrous web can alternatively always also be determined. These two values, which always add up to 100%, describe the same fact.

Frequently, the air temperature in the dryer hoods which are suitable for aspects of this invention advantageously lies between 150° C. and 500° C., in particular between 250° C. and 400° C. In steam-heated dryer hoods, the temperature seldom exceeds 200° C. For higher temperatures, gas-heated dryer hoods are usually used.

Advantageously, the determination of the dryness of the fibrous web before the drying cylinder can be carried out by the amount of water which was present in the fibrous web before the drying cylinder being determined from the amount of water at the reel-up and the amount of water which is evaporated in the dryer hood.

Since, after the drying cylinder, in particular the Yankee cylinder, often no more noticeable drying of the fibrous web takes place, this can be done, for example, by simple addition. If this determined amount of water is related to the total mass of the web, then the result is the corresponding dryness.

One possible implementation of the dryness determination can therefore appear as follows:

$$\text{Dryness} = \frac{\text{solids}\left[\frac{kg}{h}\right]}{\text{H2O(at reel} - \text{up)}\left[\frac{kg}{h}\right] + \text{H2O(evaporated)}\left[\frac{kg}{h}\right] + \text{solids}\left[\frac{kg}{h}\right]}$$

However, modifications of this balance calculation can also be used. For example, by adapting the formula, it is possible to take account of the fact that the moisture of the fibrous web can still change between the separation from the drying cylinder and the reel-up. The dryness of the web can in principle increase or else decrease at this point. This can be done, for example, by means of an empirically determined weighting factor.

In further advantageous embodiments, provision can be made for the machine to comprise measuring devices in order to acquire at least one, preferably all, the variables relating to a), b) and/or c) online during running operation of the machine.

In many applications, in particular the variable c), that is to say the amount of water evaporated in the hood or the hoods, is determined online. This can be carried out, for example, by means of measurements on the hood exhaust air. Via the exhaust air stream, for example, the volume and the mass of the exhaust air per unit time, its moisture and temperature, as well as the proportion of dry air, can be determined continuously or at regular intervals. The quantity of water carried away per unit time can then be determined therefrom. In addition, measurements in the feed air stream, which can possibly be included in the determination as well, can also be made.

Likewise, the amounts of water and solids—in particular fibers and fillers—can be determined online by means of a sensor before the reel-up.

However, it may be advantageous to determine these values via a laboratory measurement. This is because taking a sample on a wound-up reel is possible without problems or danger, and is normally carried out in any case within the context of quality control. Additionally, the values relating to a) and b) can be determined considerably more quickly from the finished web—for example via rapid ashing—than when taking a sample from the moisture web before the drying cylinder. And, finally, these values, specifically the amount of solids, do not change so quickly and so highly, so that the determination of the dryness before the drying cylinder is not influenced very highly if the values relating to a) and b) are updated only at certain intervals.

In further advantageous embodiments, still further variables can be used to determine the dryness of the fibrous web.

For example, sensors can be provided, with which the condition of a fabric, for example a felt, is monitored. In particular, the felt moisture can also be used in the determination of the dryness of the fibrous web.

With regard to the control or regulation, the object is achieved by a method for controlling or regulating a machine for producing a fibrous web, in particular a tissue web, wherein the machine comprises a drying cylinder, in particular a Yankee cylinder, to which at least one, preferably two, dryer hoods are assigned, and a reel-up for winding up the fibrous web, characterized in that the dryness of the fibrous web before the drying cylinder is used for the control or regulation.

Advantageous embodiments are described in the dependent claims.

Thus, it may in particular be advantageous if the dryness of the fibrous web is determined online during the operation of the machine. Since the direct measurement of the dryness is difficult, in particular an indirect determination of the dryness can be carried out and used for the control. Usually, for this indirect determination, use is made of measured values which are already present in any case for the operator of the machine. Thus, the control or regulation can be implemented particularly economically and without great outlay.

It is very particularly advantageous if a method for determining the dryness of the fibrous web according to the invention is used for the determination of the dryness before the drying cylinder.

In an advantageous embodiment, provision can be made for the temperature of the at least one dryer hood—in particular all the dryer hoods of the drying cylinder—to be controlled or regulated as a function of the dryness of the fibrous web before the drying cylinder. Thus, for example, with a lower dryness of the fibrous web before the drying cylinder, the temperature of the hood air can be increased, which improves the drying.

In a further advantageous embodiment, provision can be made for at least one fabric, in particular a felt, to be provided in the machine, and for the conditioning of this fabric to be controlled or regulated as a function of the dryness of the fibrous web before the drying cylinder.

Frequently, the fibrous web is guided to the drying cylinder supported on such a fabric or such a felt. For conditioning the fabric, water can be applied to the fabric—for example by means of high-pressure spray pipes. As a result, amongst other things contaminants can be removed from the fabric. Likewise, suction devices are usually provided for the conditioning, in order to remove excess water from the fabric.

The denser the felt becomes, the more poorly—under otherwise equal conditions—the dryness of the fibrous web before the drying cylinder will be. The dryness then serves as a type of indicator for the condition of the felt. Via the determined dryness it would then be possible, for example, for the amount of water and/or the water pressure on a high-pressure spray pipe to be regulated, and therefore for the cleaning of the felt to be optimized. Thus, in this embodiment, it is possible to dispense with a sensor for determining the felt condition.

Advantageously, still further values can also be used for this regulation, in order for example to ensure that the changed dryness has not arisen because of a change in raw material or changed machine settings, such as vacuums on suction devices.

In a further advantageous embodiment, provision can be made for the dosing of a chemical, in particular a release agent, to be controlled or regulated as a function of the dryness of the fibrous web before the drying cylinder. These release agents are generally sprayed onto the drying cylinder, in order to facilitate the separation or creping of the fibrous web off the cylinder surface. These chemicals represent a cost factor. Since the moisture of the fibrous web has a considerable influence on the adhesive behavior of the web to the cylinder, the amount of release agent can be adapted optimally to the web conditions as a result of the knowledge of the moisture before the drying cylinders. Expensive over-dosing of the release agent can be avoided as a result.

In many embodiments, three chemicals are applied to the Yankee in a specific mixture ratio. These are "base", "modifier" and release agent, the base forming the base layer or protective layer for the Yankee surface, the modifier determining the time in which the coating cures, and the release agent to influence or to vary this time.

The chemicals are diluted with water and applied to the cylinder surface, normally between creping doctor and press nip. If this amount of water is too high, this can have a detrimental influence on the dryness.

In all the methods and embodiments described in this application, provision can frequently be made for the fibrous web to pass through a press nip before the drying cylinder or directly on the drying cylinder, wherein the press nip can in particular be a shoe press nip.

In many embodiments, the fibrous web runs together with a felt through a press nip which is formed from a press roll and a Yankee cylinder as a mating roll. By means of this press nip, the fibrous web is then transferred from the felt to the Yankee cylinder. In such an embodiment, taking a sample close before the Yankee cylinder is particularly difficult, specifically both with regard to endangering the personnel and also with regard to damaging the cylinder surface and/or the felt. Therefore, the method according to one aspect of the invention is particularly advantageous here, since no sample has to be taken directly before the drying cylinder for this purpose.

In addition, a computer program for carrying out a method according to the invention, and a computer program product having such a computer program are provided.

It may be advantageous if such a computer program is executed on a computer and can make access to data from the control and management systems of the machine (DCS—distributed control system, QCS—quality-control system). There, much of the data which is needed to carry out a method as claimed in one aspect of the invention, for example the amounts of exhaust air, temperature and moisture of the hood exhaust air or measured values for the properties of the fibrous web at the reel-up, is frequently already acquired. These values can then be provided by these systems in order to carry out the method.

BRIEF DESCRIPTION OF THE SINGLE VIEW OF THE DRAWING

The FIGURE shows a detail, not to scale, from a machine for carrying out a method according to one aspect of the invention.

DETAILED DESCRIPTION OF THE INVENTION

The FIGURE shows a detail from a machine 1 for producing a tissue web 2. The tissue web 2, coming from a headbox, is transported and supported on a felt 5. A press nip 7 is provided, which is formed from a press roll 6 and a Yankee cylinder 3 as a mating roll. The press roll 6 can be a shoe press roll 6. However, the press nip 7 can also be a conventional roll nip 7. In the press nip 7, the fibrous web 2 is transferred to the Yankee cylinder 3. After that, the felt 5 is guided back again without the tissue web 3. In the region of this return, further devices 40 for felt conditioning can be provided, such as spray pipes or suction devices. Likewise, measuring devices for the felt condition can be provided.

The Yankee cylinder 3 is usually steam-heated. In the machine 1 shown in the FIGURE, a dryer hood 4 is assigned to the Yankee cylinder 3. In other advantageous embodiments, two dryer hoods 4 can also be provided. These are then arranged directly one after the other as a rule and are designated by wet part and dry part. After leaving the dryer hood 4, the material web 2 is separated or creped off the Yankee cylinder at the separation point 8 and led onward in the direction of the reel-up 10. To facilitate the removal of the tissue web 2 from the Yankee cylinder 3, a release agent can be applied to the surface of the Yankee cylinder 3. The application can be carried out, for example, by a spray applicator 50 and is expediently done in the region of the Yankee cylinder 3 which is not covered by the tissue web 2, that is to say between the separation point 8 and the press nip.

The dryer hood 4 in the machine in the FIGURE extends over a very large part of the surface of the Yankee cylinder 3. By means of said hood, hot air is led onto the fibrous web 2. In general, the air temperature in the dryer hoods 4 which are suitable for aspects of this invention can advantageously lie between 150° C. and 500° C., in particular between 250° C. and 400° C. as measured by a device 30 for measuring the temperature of the dryer hood. In steam-heated dryer hoods 4, the temperature seldom exceeds 200° C. For higher temperatures, gas-heated dryer hoods are usually used. As a result of the drying of the tissue web 2, moisture escapes from the tissue web 2 and passes into the dryer hood 4 and is enriched therein. For this reason, part of this moist hood air is normally led away as exhaust air and dry air is fed to the dryer hood 4 as feed air. A device 20a measures an amount of solids in the fibrous web, a device 20b measures an amount of water in the fibrous web and a device 20c measures an amount of water evaporated in the dryer hood or hoods. By means of measurements in the exhaust air stream—and possibly in the feed air stream—the amount of water carried along with the exhaust air per unit time can be determined online very reliably during the running operation of the machine 1 and, to a very good approximation, corresponds to the amount of water removed from the tissue web by drying in said time. The knowledge of this variable is an important variable for the performance of the method as claimed in some aspects of the invention. Together with the knowledge of the amount of water and the amount of solids (fibers, fillers etc) of the tissue web 2 at the reel-up, or a sufficiently good approximation thereto, the dryness of the fibrous web after the press nip 7 or at the entry into the dryer hood 4 can be determined to a very good approximation. (These two points lie very close to each other in the embodiment according to the FIGURE, which means that, amongst other things, taking a sample of the tissue web 2 in this region is very difficult and dangerous.

The online available dryness before the Yankee cylinder 3 can be used for various controls and regulations.

Thus, for example, the temperature of the hood air of the at least one dryer hood 4 can be controlled or regulated as a function of the dryness of the fibrous web 2 before the drying cylinder 3. Said temperature can advantageously lie in the range between 205° C. and 360° C.

Alternatively or additionally, the dosing of a chemical, in particular a release agent, can be controlled or regulated as a function of the dryness of the fibrous web 2 before the drying cylinder 3.

Alternatively or additionally, the conditioning of a fabric 5 can be controlled or regulated as a function of the dryness of the fibrous web 2 before the drying cylinder 3.

These examples of regulations constitute advantageous embodiments. However, the invention is not restricted to the regulations described.

The invention claimed is:

1. A method for determining the dryness of a fibrous web or a tissue web during the production of the fibrous web in a machine, the method comprising the following steps:
   providing a machine including a drying cylinder or Yankee cylinder, at least one dryer hood associated with the drying cylinder, and a reel-up for winding up the fibrous web; and
   determining the dryness of the fibrous web before the drying cylinder based on measured values describing the following variables:
   a) an amount of solids in the fibrous web at the reel-up;
   b) an amount of water in the fibrous web at the reel-up; and
   c) an amount of water evaporated in the at least one dryer hood.

2. The method according to claim 1, which further comprises using measuring devices of the machine to acquire at least one of the variables a), b) or c) online during a running operation of the machine.

3. The method according to claim 1, which further comprises also taking into account a moisture of a felt transferring the fibrous web to the drying cylinder when performing the step of determining the dryness of the fibrous web.

4. A method for controlling or regulating a machine for producing a fibrous web or a tissue web, the method comprising the following steps:
   providing a machine including a drying cylinder or Yankee cylinder, at least one dryer hood associated with the drying cylinder, and a reel-up for winding up the fibrous web;
   determining a dryness of the fibrous web before the drying cylinder based on measured values describing the following variables:
   a) an amount of solids in the fibrous web at the reel-up,
   b) an amount of water in the fibrous web at the reel-up, and
   c) an amount of water evaporated in the dryer hood or hoods; and
   using the dryness of the fibrous web before the drying cylinder for controlling or regulating the machine.

5. The method according to claim 4, which further comprises determining the dryness of the fibrous web online during operation of the machine.

6. The method according to claim 4, which further comprises controlling or regulating a temperature of the at least one dryer hood as a function of the dryness of the fibrous web before the drying cylinder.

7. The method according to claim 4, which further comprises providing at least one fabric in the machine, and controlling or regulating a conditioning of the fabric as a function of the dryness of the fibrous web before the drying cylinder.

8. The method according to claim 4, which further comprises controlling or regulating a dosing of a chemical or a release agent as a function of the dryness of the fibrous web before the drying cylinder.

9. The method according to claim 4, which further comprises guiding the fibrous web through a press nip or a shoe press nip before the drying cylinder or directly on the drying cylinder.

* * * * *